United States Patent
Kurnik

(10) Patent No.: US 7,844,403 B2
(45) Date of Patent: Nov. 30, 2010

(54) TEMPERATURE STEP CORRECTION WITH DOUBLE SIGMOID LEVENBERG-MARQUARDT AND ROBUST LINEAR REGRESSION

(75) Inventor: Ronald T. Kurnik, Foster City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1126 days.

(21) Appl. No.: 11/458,644

(22) Filed: Jul. 19, 2006

(65) Prior Publication Data

US 2008/0033701 A1    Feb. 7, 2008

Related U.S. Application Data

(63) Continuation-in-part of application No. 11/349,550, filed on Feb. 6, 2006, now Pat. No. 7,680,868, which is a continuation-in-part of application No. 11/316,315, filed on Dec. 20, 2005, now Pat. No. 7,668,663.

(51) Int. Cl.
*G01N 33/48* (2006.01)
(52) U.S. Cl. ......................................................... 702/19
(58) Field of Classification Search .................... 702/19
See application file for complete search history.

(56) References Cited

U.S. PATENT DOCUMENTS

| 2007/0143070 A1 | 6/2007 | Kurnik et al. |
| 2007/0143385 A1 | 6/2007 | Kurnik et al. |
| 2007/0148632 A1 | 6/2007 | Kurnik |

FOREIGN PATENT DOCUMENTS

| WO | WO 97/46707 A2 | 12/1997 |
| WO | WO 97/46707 A3 | 12/1997 |
| WO | WO 97/46712 A2 | 12/1997 |
| WO | WO 97/46712 A3 | 12/1997 |
| WO | WO 97/46714 A1 | 12/1997 |

OTHER PUBLICATIONS

Bieche, I. et al., "Quantitation of *MYC* Gene Expression in Sporadic Breast Tumors With a Real-Time Reverse Transcription-PCR assay," *Cancer Research*, Jun. 15, 1999, vol. 59, pp. 2759-2765.
Cambridge University Press, "Root Finding and Nonlinear Sets of Equations," Chapter 9 in *Numerical Recipes in C: The Art of scientific Computing*, 1988-1992, pp. 347-369.
Gibson, U.E.M. et al., "A Novel Method for Real Time Quantitative RT-PCR," *Genome Research*, 1996, vol. 6, pp. 995-1001.
Kurnik, R.T. et al., "Application of the Mixtures of Experts Algorithm for Signal Processing in a Noninvasive Glucose Monitoring System," *Sensors and Actuators B*, 1999, vol. 60, pp. 19-26.
Lourakis, M.I.A., "A Brief Descritption of the Levenberg-Marquardt Algorithm Implemened by levmar," Feb. 11, 2005, pp. 1-6.
McLauchlan, P., "Robust Observations," located at <http://gandalf-library.sourceforge.net/tutorial/report/node131.html>, Mar. 17, 2006, last visited on Jan. 25, 2008, 2 pages.
Motulsky, H. et al., *Fitting Models to Biological Data Using Linear and Nonlinear Regression, Version 4.0*, GraphPad Software, Inc., 2003, pp. 3-11 (Table of Contents Only).
Motulsky, H., *Statistics Guide Statistical Analyses for Laboratory and Clinical Researchers, Version 4.0*, GraphPad Software, Inc., Feb. 2005, 6 pages (Table of Contents Only).
Wang, S-S. et al., "Homogeneous Real-Time Detection of Single-Nucleotide Polymorphisms by Strand Displacement Amplification on the BD ProbeTec ET System," *Clinical Chemistry*, 2003, vol. 49, No. 10, pp. 1599-1607.
Weisstein, E., "Cubic Spline," located at <http://mathwolrd.wolfram.com/CubicSpline.html>, 1999, last visited on Jan. 25, 2008, 4 pages.
Weusten, J.J.A.M. et al., "Principles of Quantitation of Viral Loads Using Nucleic Acid Sequence-Based Amplification in Combination With Homogeneous Detection Using Molecular Beacons," *Nucleic Acids Research*, 2002, vol. 30, No. 6, e26, 7 pages.

*Primary Examiner*—Jerry Lin
(74) *Attorney, Agent, or Firm*—Townsend and Townsend and Crew LLP; Gerald T. Gray

(57) ABSTRACT

Systems and methods for improving Ct determination in PCR amplification curves by correcting PCR data for temperature shifts that may occur during the PCR process. A double sigmoid function with parameters determined by a Levenberg-Marquardt (LM) regression process is used to find an approximation to the portion of the curve in the region after the temperature shift, termed "CAC", the cycle where the temperature shift occurred. A robust linear approximation is determined for the portion of the curve in the region before the temperature shift. Values of the fluorescent intensity for the cycle CAC or CAC+1 are determined using both the linear approximation and the LM process, and a difference in these values is subtracted off of the portion of the data set representing the portion of the curve before the temperature shift occurred to produce a shift-corrected data set. The shift-corrected data set may be displayed or otherwise used for further processing.

36 Claims, 15 Drawing Sheets

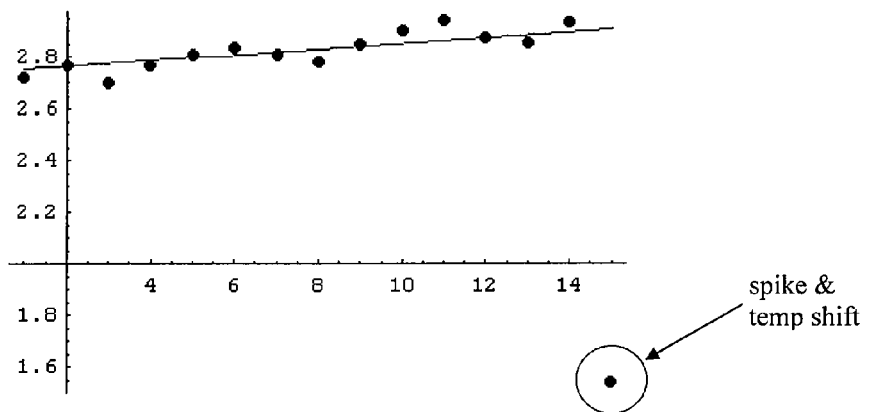
FIG. 4A: Robust Linear Estimation
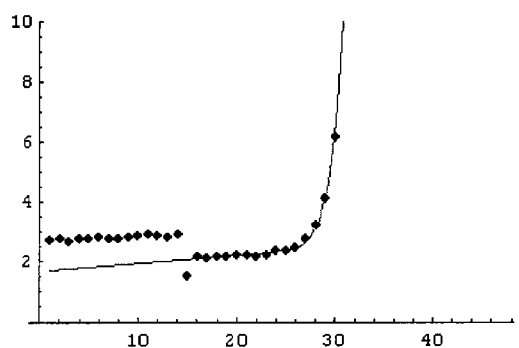
FIG. 4B: Robust Double Sigmoid Estimation

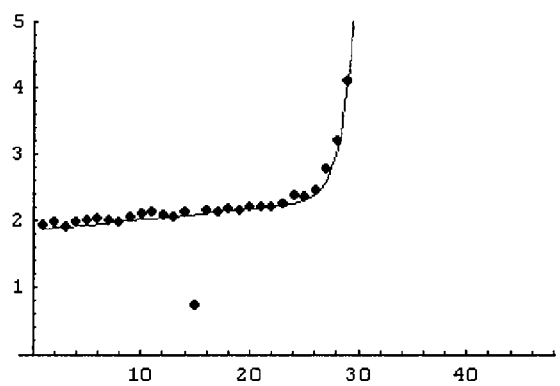
FIG. 4C: Temperature Shift Corrected Data
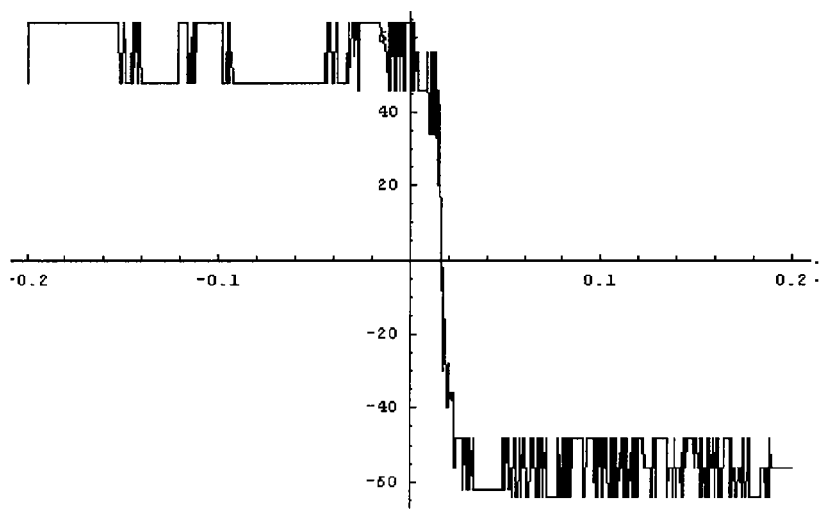
FIG. 5

FIG. 6: Spike identification and replacement process flowchart

This flowchart models the Levenberg-Marquardt outlier method
File: LMOM_SpikeDetector.cs
Class: LMOM_SpikeDetector
Function: CorrectSpikes
Lines: 256-555

The equation used to model PCR curves is a double sigmoid:
$a + bx + c / (1+\mathrm{Exp}(-d*(x-e))) (1+\mathrm{Exp}(-f*(x-g)))$ Variables Summary a: 1st parameter of the double sigmoid equation
b: 2nd parameter of the double sigmoid equation
c: 3rd parameter of the double sigmoid equation
d: 4th parameter of the double sigmoid equation
e: 5th parameter of the double sigmoid equation
f: 6th parameter of the double sigmoid equation
g: 7th parameter of the double sigmoid equation
MAPETreshold: Cutoff for the MAPE value of a curve fit to be considered valid
ziTreshold1: Cutoff value for the Z-Value of a point to be considered a spike
ziTreshold2: Cutoff value for the Z-Value of a point to be considered a big spike 502 — Set Parameters b, d and f.
- Do/ Set (d,f) = (0.1,0.7), (1.0,0.4), (0.35,0.25)
- Do/ Set b =0.01 for all inital parameter sets.

These parameters don't depend on the curve.

504 — Set Parameters a and c
- Do/ Set a = 3rd lowest Y-Value for every set of initial parameters.
- Do/ Set c = 3rd highest Y-Value -a for the two first sets of initial parameters.
- Do/ Set c = 3rd highest Y-Value-a+2 for the last set of initial parameters.

These parameters depend on the curve and require minimum calculation.

506 — Set Parameters e and g

These parameters depend on the curve and require more calculation.

510 — Set the LM with the initial set of parameters.

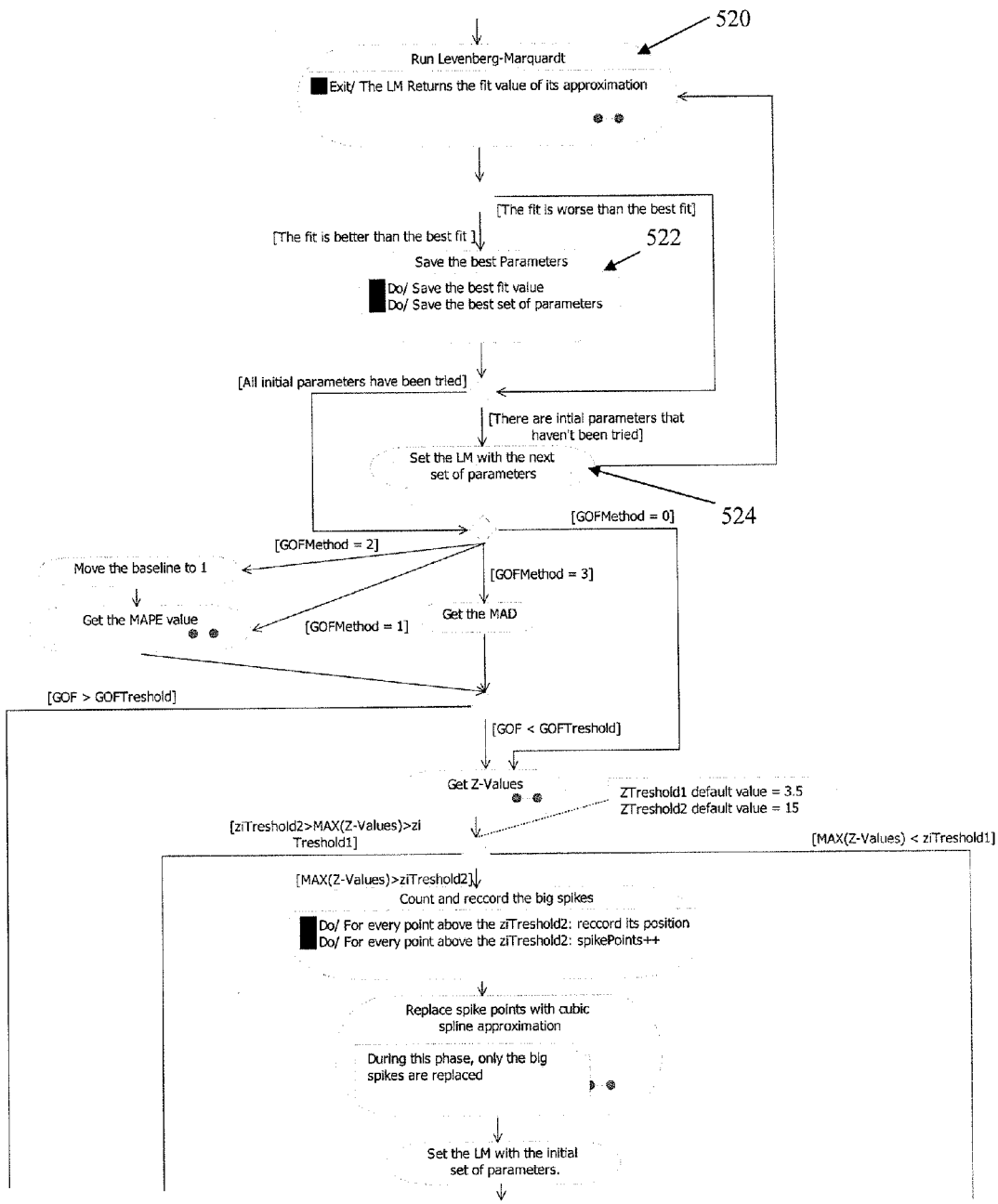
FIG. 6 (cont. p.2)

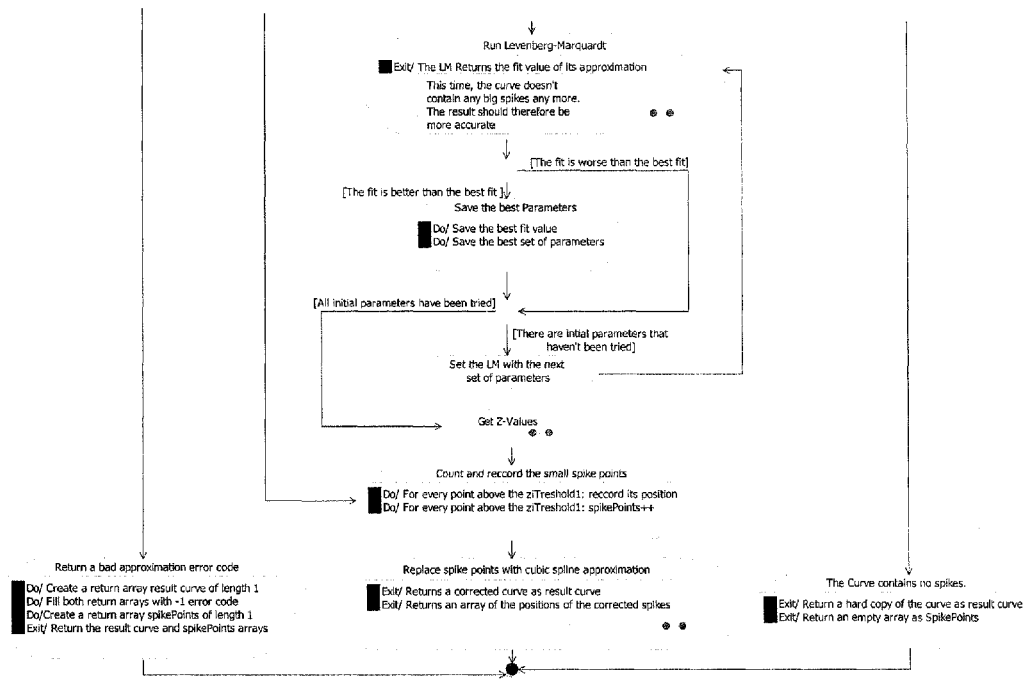
FIG. 6 (cont. p.3)

FIG. 7: Double sigmoid decomposition
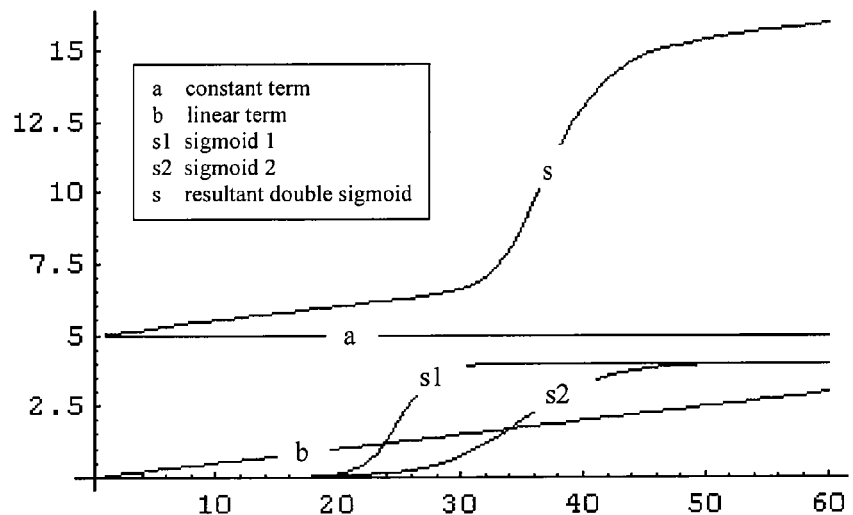
FIG. 8: The parameters of a sigmoid
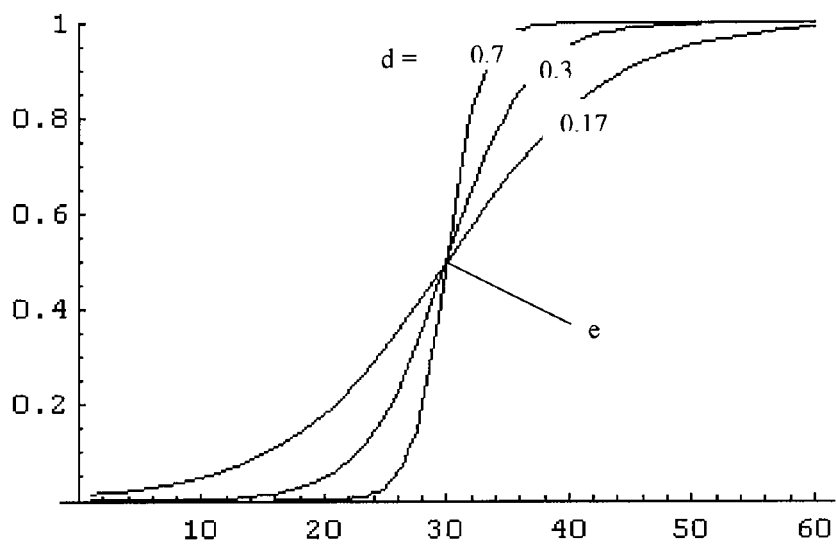

FIG. 9: Initial parameters shapes
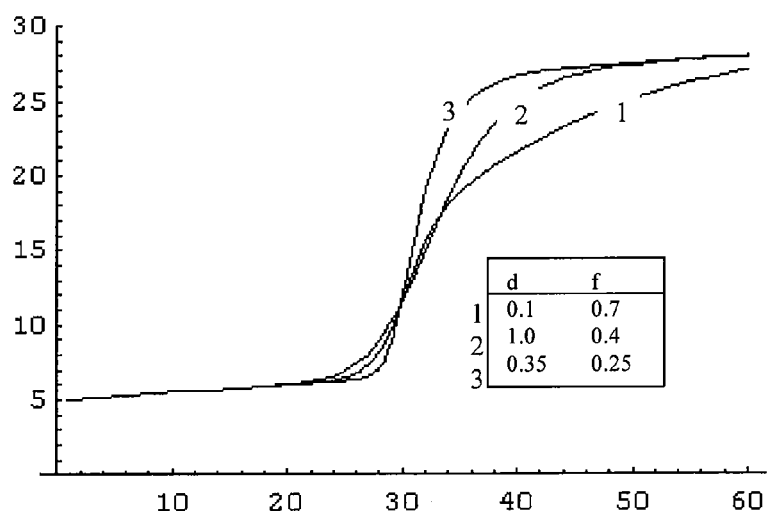

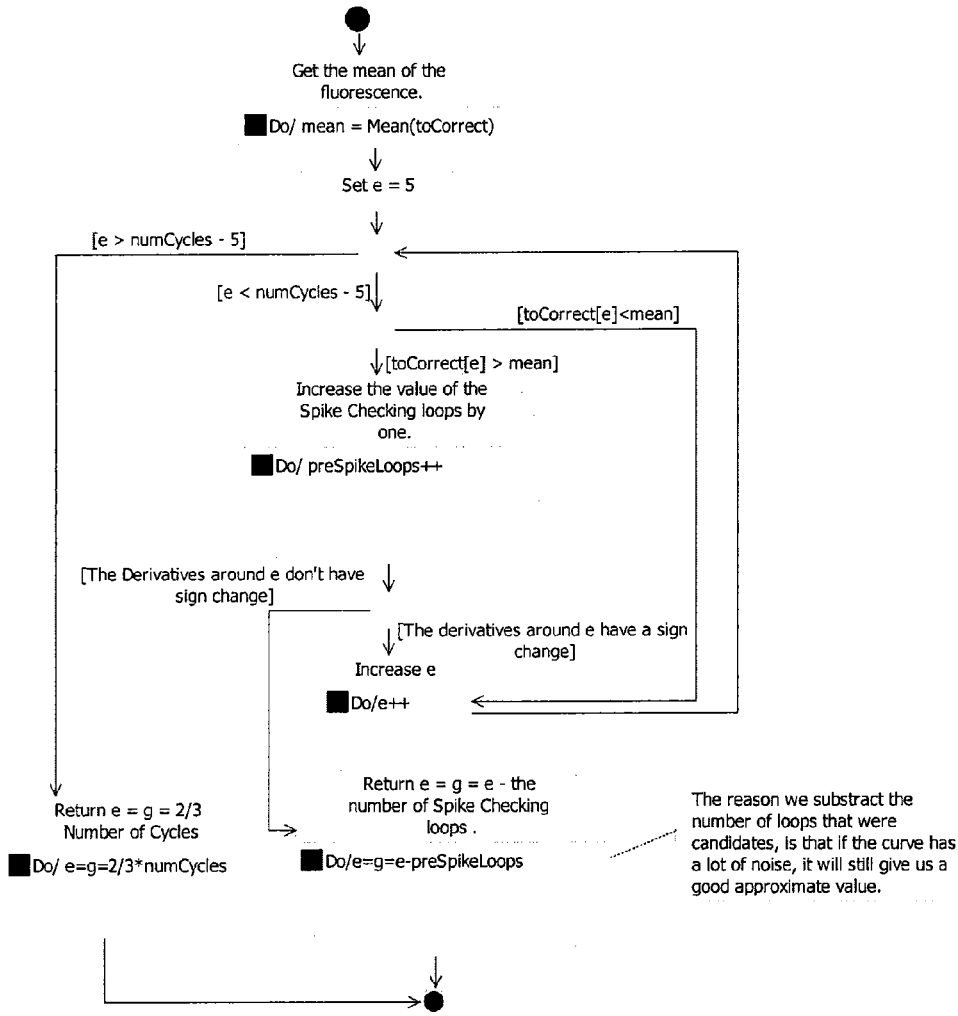
FIG. 10: Parameter e and g calculation flowchart

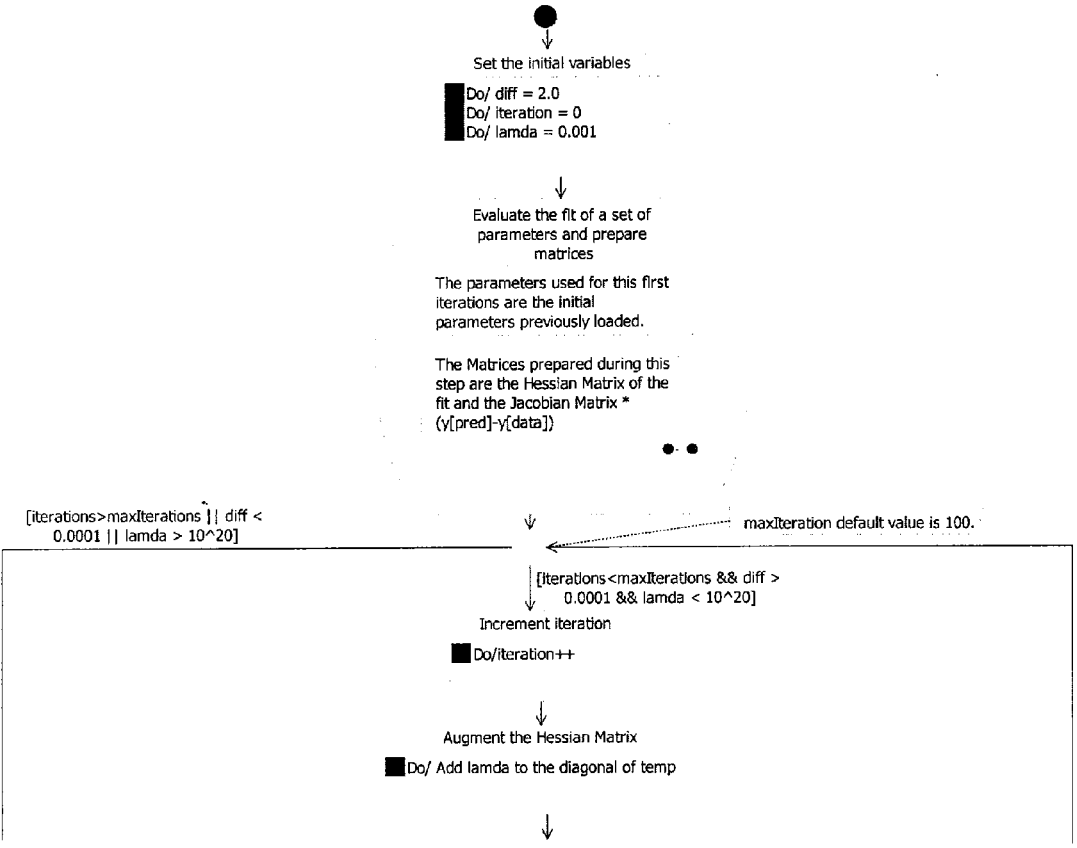
FIG. 11: Levenberg-Marquardt Process flowchart

TEMPERATURE STEP CORRECTION WITH DOUBLE SIGMOID LEVENBERG-MARQUARDT AND ROBUST LINEAR REGRESSION

CROSS-REFERENCES TO RELATED APPLICATIONS

This application is a continuation-in-part (CIP) of the U.S. application Ser. No. 11/349,550, filed Feb. 6, 2006, entitled "PCR ELBOW DETERMINATION BY USE OF A DOUBLE SIGMOID FUNCTION CURVE FIT WITH THE LEVENBERG-MARQUARDT ALGORITHM AND NORMALIZATION," which is a continuation-in-part (CIP) of the U.S. application Ser. No. 11/316,315, filed Dec. 20, 2005, titled "LEVENBERG-MARQUARDT OUTLIER SPIKE REMOVAL METHOD," which are hereby incorporated by reference in their entirety.

BACKGROUND OF THE INVENTION

The present invention relates generally to systems and methods for processing data representing sigmoid or growth curves, and more particularly to systems and methods for correcting for temperature shifts and for determining characteristic cycle threshold (Ct) or elbow values in PCR amplification curves.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in the process to facilitate detection and quantification of the amplification process.

A typical real-time PCR curve is shown in FIG. 1, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labelled hybridization probes which only emit fluorescence signals when they are bound to the target nucleic acid or in certain cases also by means of fluorescent dyes that bind to double-stranded DNA.

For a typical PCR curve, identifying a transition point at the end of the baseline region, which is referred to commonly as the elbow value or cycle threshold (Ct) value, is extremely useful for understanding characteristics of the PCR amplification process. The Ct value may be used as a measure of efficiency of the PCR process. For example, typically a defined signal threshold is determined for all reactions to be analyzed and the number of cycles (Ct) required to reach this threshold value is determined for the target nucleic acid as well as for reference nucleic acids such as a standard or housekeeping gene. The absolute or relative copy numbers of the target molecule can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). The elbow value in region 20 at the end of the baseline region 15 in FIG. 1 would be in the region of cycle number 30.

In some PCR assays, such as HIV assays, there is typically a change in the annealing temperature during the PCR reaction. This temperature change causes a subsequent shift in the fluorescence signal at the cycle number where the temperature change occurs. Accordingly, it is necessary to correct for this signal change in order to calculate a correct Ct value. The cycle at which the temperature change occurs is known and it would be a simple matter to correct for this temperature shift if the baseline were perfectly flat and has no spikes. Unfortunately, the baseline if often sloped and may also contain signal spikes (outliers) at any position. If a spike occurs at the temperature change position, it is even more difficult to correct the baseline curve.

Therefore it is desirable to provide systems and methods for determining the elbow value in curves, such as sigmoid-type or growth curves, and PCR curves in particular, which overcome the above and other problems. In particular, the systems and methods should implement temperature step correction in a manner that is reliable and robust to artifacts such as outliers.

BRIEF SUMMARY OF THE INVENTION

The present invention provides systems and methods for improving Ct determination in PCR amplification curves by correcting PCR data for temperature shifts that may occur during the PCR process.

According to one aspect, a double sigmoid function with parameters determined by a Levenberg-Marquardt (LM) regression process is used to find an approximation to the portion of the curve in the region after the temperature shift, termed "CAC", the cycle where the temperature shift occurred. A robust linear approximation is determined for the portion of the curve in the region before the temperature shift. Values of the fluorescent intensity for the cycle CAC or CAC+1 are determined using both the linear approximation and the LM process, and a difference in these values is subtracted off of the portion of the data set representing the portion of the curve before the temperature shift occurred to produce a shift-corrected data set. The shift-corrected data set is then returned and may be displayed or otherwise used for further processing.

According to one aspect of the present invention, a computer-implemented method is provided for correcting for temperature step changes in a data set for a Polymerase Chain Reaction (PCR) growth curve having a baseline portion and a growth portion. The method typically includes receiving a data set for a PCR growth curve, wherein the data set includes a plurality of data points for a kinetic Polymerase Chain Reaction (PCR) process, each data point having a pair of coordinate values (x,y), wherein x represents the cycle number and y represents an accumulation of amplified polynucleotide. The method also typically includes calculating a linear approximation to a first portion of the curve, the first portion including data points in the data set including cycle numbers less than or equal to a cycle number (CAC) at which an annealing temperature change occurs in the PCR process, and calculating an approximation to a second portion of the curve by applying a Levenberg-Marquardt (LM) regression process to a second portion of the data set and a double sigmoid function to determine parameters of the function, the second portion of the data set including data points having cycle numbers greater than the CAC. The method also typically includes estimating a first y value for a first x value using the linear approximation of the first portion of the curve, estimating a second y value for the first x value using the approximation calculated for the second portion of the curve, determining a difference between the first and second y values, and subtracting off the difference from each y value for the data points corresponding to the first portion of the curve to produce a modified data set. In certain aspects, the first x value is the CAC. In other aspects, the first x value is CAC+1.

According to another aspect of the present invention, a computer-readable medium is provided that includes code for controlling a processor to correct for temperature step changes in a data set for a Polymerase Chain Reaction (PCR) growth curve having a baseline portion and a growth portion. The code typically includes instructions to receive a data set for a PCR growth curve, wherein the data set includes a plurality of data points for a kinetic Polymerase Chain Reaction (PCR) process, each data point having a pair of coordinate values (x,y), wherein x represents the cycle number and y represents an accumulation of amplified polynucleotide. The code also typically includes instructions to calculate a linear approximation to a first portion of the curve, the first portion including data points in the data set including cycle numbers less than or equal to a cycle number (CAC) at which an annealing temperature change occurs in the PCR process, and calculate an approximation to a second portion of the curve by applying a Levenberg-Marquardt (LM) regression process to a second portion of the data set and a double sigmoid function to determine parameters of the function, the second portion of the data set including data points having cycle numbers greater than the CAC. The code also typically includes instructions to estimate a first y value for a first x value using the linear approximation of the first portion of the curve, estimate a second y value for the first x value using the approximation calculated for the second portion of the curve, determine a difference between the first and second y values, and subtract off the difference from each y value for the data points corresponding to the first portion of the curve to produce a modified data set. In certain aspects, the first x value is the CAC. In other aspects, the first x value is CAC+1.

According to yet another aspect of the present invention, a kinetic Polymerase Chain Reaction (PCR) system is provided that typically includes a kinetic PCR analysis module that generates a PCR data set representing a kinetic PCR amplification curve having a baseline portion and a growth portion, wherein the data set includes a plurality of data points, each data point having a pair of coordinate values (x,y), wherein x represents the cycle number and y represents an accumulation of amplified polynucleotide, and an intelligence module adapted to process the PCR dataset to correct for temperature step changes in the data set, by calculating a linear approximation to a first portion of the curve, the first portion including data points in the data set including cycle numbers less than or equal to a cycle number (CAC) at which an annealing temperature change occurs in the PCR process, and calculating an approximation to a second portion of the curve by applying a Levenberg-Marquardt (LM) regression process to a second portion of the data set and a double sigmoid function to determine parameters of the function, the second portion of the data set including data points having cycle numbers greater than the CAC. The intelligence module is typically also adapted to estimate a first y value for a first x value using the linear approximation of the first portion of the curve, estimate a second y value for the first x value using the approximation calculated for the second portion of the curve, determine a difference between the first and second y values, and subtract off the difference from each y value for the data points corresponding to the first portion of the curve to produce a modified data set. In certain aspects, the first x value is the CAC. In other aspects, the first x value is CAC+1.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 4A shows an example of a linear approximation for the portion of the data set from cycle 1 to cycle CAC for a PCR data set having a temperature shift. FIG. 4B shows an example of an approximation for the portion of the data set from cycle CAC+1 to the end cycle for the PCR data set of FIG. 4A where the approximation is determined using a LM regression process to determine the parameters of a double sigmoid function according to the present invention. FIG. 4C shows an example of the temperature shift corrected data for the data set shown in FIGS. 4A and 4B.

FIG. 5 illustrates a typical shape of the function used in the bisection method according to aspects of the present invention FIG. 6 illustrates a detailed process flow for a spike identification and replacement process according to one embodiment of the present invention.

FIG. 7 illustrates a decomposition of the double sigmoid equation including parameters a-g. Parameters a-g define the shape and position of a double sigmoid curve.

FIG. 8 shows the influence of parameter (d) on the curve and the position of (e), the x value of the inflexion point. All curves in FIG. 8 have the same parameter values except for parameter d.

FIG. 9 shows an example of the three curve shapes for the different parameter sets.

FIG. 10 illustrates a process for determining the value of double sigmoid equation parameters (e) and (g) according to one aspect.

DETAILED DESCRIPTION OF THE INVENTION

The present invention provides systems and methods for correcting PCR amplification curves for temperature shifts that may occur during the PCR process. One example of a temperature shift is a controlled change in the annealing temperature at a certain cycle during the assay. Typically this temperature shift occurs during a portion of the process represented by the baseline region. This temperature change causes a subsequent shift in the fluorescent signal at the cycle number where the shift occurred. The cycle where the temperature shift occurred will be referred to herein as the CAC, for cycle of annealing change. In certain aspects, a double sigmoid function with parameters determined by a Levenberg-Marquardt (LM) regression process is used to find an approximation to the portion of the curve in the region after the temperature shift. A robust linear approximation is determined for the portion of the curve in the region before the temperature shift. Values of the fluorescent intensity for the cycle CAC+1 are determined using both the linear approximation and the LM process, and a difference in these values is then subtracted off of the portion of the data set representing the portion of the curve before the temperature shift occurred to produce a shift-corrected data set. The shift-corrected data set is then returned and may be displayed or otherwise used for further processing. For example, the shift-corrected data set can be used to determine the Ct value of the PCR assay. Also, the corrected data set can be processed to remove any spikes that may be present in the portion of the data set that was processed to determine a robust linear approximation.

Figure 1:
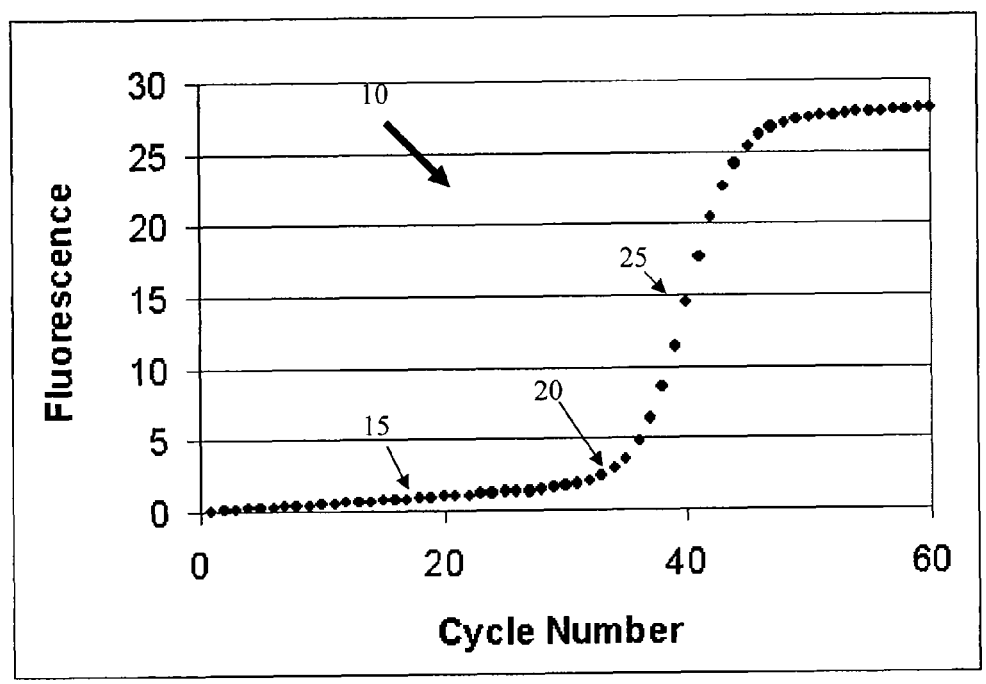
FIG. 1 illustrates an example of an amplification curve in the context of a PCR process.

One example of an amplification curve 10 in the context of a PCR process is shown in FIG. 1. As shown, the curve 10 includes a lag phase region 15, and an exponential phase region 25. Lag phase region 15 is commonly referred to as the baseline or baseline region. Such a curve 10 includes a transitionary region of interest 20 linking the lag phase and the exponential phase regions. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process. In a typical PCR curve, identifying a transition point referred to as the elbow value or cycle threshold (Ct) value is useful for understanding efficiency characteristics of the PCR process.

Other processes that may provide similar sigmoid or growth curves include bacterial processes, enzymatic processes and binding processes. In bacterial growth curves, for example, the transition point of interest has been referred to as the time in lag phase, θ. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System", Clin Chem 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons", Nucleic Acids Research, 2002 30(6):26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, as shown in FIG. 1, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of abundance or accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

Figure 2A:
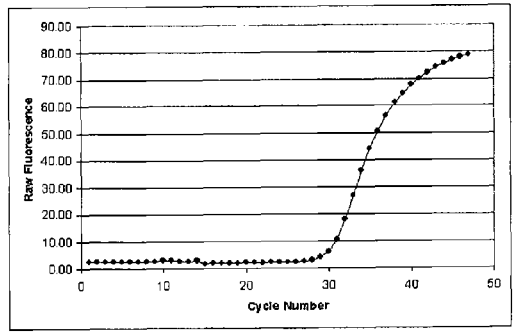
FIGS. 2A and 2B (expanded scale) show an example of a PCR curve with a temperature shift at cycle 15, together with a spike at cycle 14.
Figure 2B:
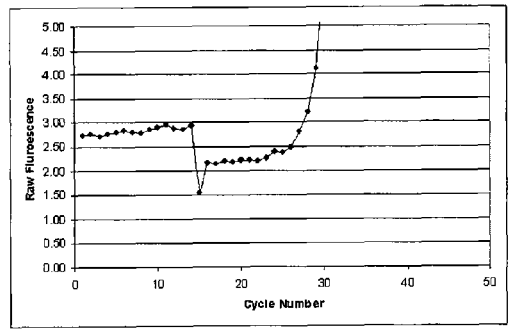
Figure 2C:
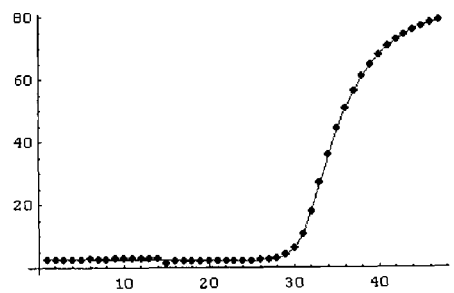
FIGS. 2C and 2D (expanded scale) show a fit resulting from a LM regression process used to process the entire PCR data set.
Figure 2D:
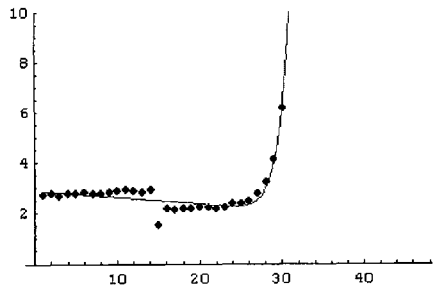
Figure 2E:
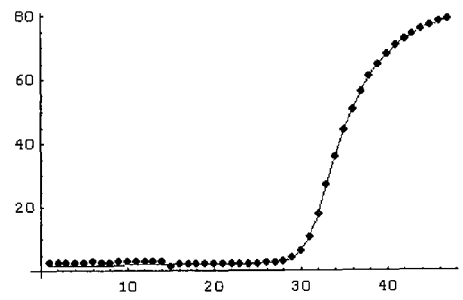
FIGS. 2E and 2F show the resultant curve fit at full scale and expanded scale when the data points from cycle 16 to the last cycle are used in the LM regression.
Figure 2F:
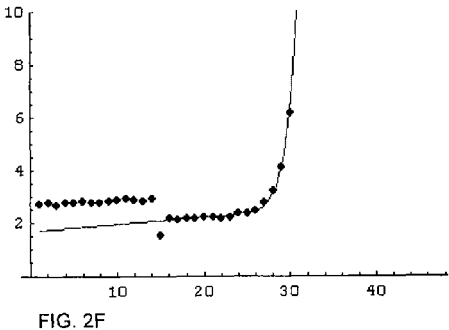

FIGS. 2A and 2B (expanded scale) show an example of a PCR curve with a temperature shift at cycle 15, together with a spike at cycle 14. If a regression process, e.g., LM regression process, is used to process the entire PCR data set, the overall fit of the double sigmoid to the data would look as shown in FIGS. 2C and 2D (expanded scale). FIGS. 2C and 2D indicate that the double sigmoid fits the data points overall, but of course may not in a satisfactory manner handle the discontinuity at CAC, the cycle where the annealing temperature change occurs. In this example, the CAC is cycle 15. If instead, the data points from cycle 16 to the last cycle are used in the LM regression, the resultant curve fit at full scale and expanded scale curve is shown in FIGS. 2E and 2F respectively. The curve fit in FIG. 2F is now much better for the data set from CAC+1 to the end than that of FIG. 2D, where the entire data set was used.

General Process Overview

Figure 3:
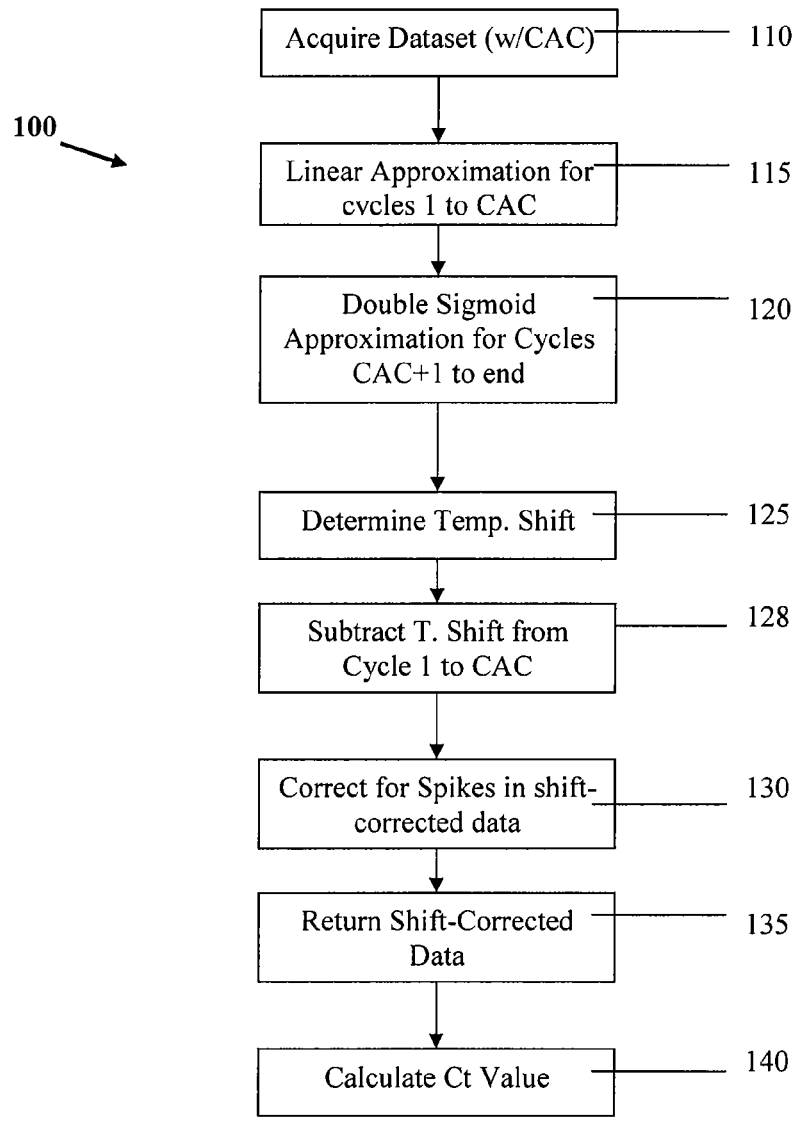
FIG. 3 illustrates one embodiment of a process for correcting for a temperature shift and determining a transitionary value in a single sigmoid curve, such as the elbow value or Ct value of a kinetic PCR amplification curve.

According to the present invention, one embodiment of a process 100 for correcting for a temperature shift and determining a transitionary value in a single sigmoid curve, such as the elbow value or Ct value of a kinetic PCR amplification curve, can be described briefly with reference to FIG. 3. In step 110, an experimental data set representing the curve is received or otherwise acquired. The cycle at which a temperature shift occurred is also identified. Typically this cycle value is known a priori, e.g., recorded by the device or instrument providing the data. An example of a plotted PCR data set is shown in FIG. 1, where the y-axis and x-axis represent fluorescence intensity and cycle number, respectively, for a PCR curve. In certain aspects, the data set should include data that is continuous and equally spaced along an axis.

In the case where process 100 is implemented in an intelligence module (e.g., processor executing instructions) resident in a PCR data acquiring device such as a thermocycler, the data set may be provided to the intelligence module in real time as the data are being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For PCR data, the pair of coordinate values typically represents the cycle number and the fluorescence intensity value. After the data set has been received or acquired in step 110, the data set may be further analyzed, e.g., to correct for temperature shifts during the assay and to determine the end of the baseline region.

In step 115, a linear robust approximation is computed on the data points from cycle 1 to cycle CAC. FIG. 4A shows an example of a linear approximation for the portion of the data set from cycle 1 to cycle CAC for a PCR data set having a temperature shift. This robust linear approximation is used to estimate the fluorescence level at CAC+1, e.g., via extrapolation. In step 120, an approximation of the portion of the curve after the CAC value, e.g., the amplification portion of the curve, is calculated. During this step, in one embodiment, a double sigmoid function with parameters determined by a Levenberg-Marquardt (LM) regression process or other regression process is used to find an approximation of a curve representing the portion of the data set from cycle CAC+1 to the last cycle in the data set. The approximation is said to be "robust" as outlier or spike points have a minimal effect on the quality of the curve fit. FIG. 4B shows an example of an approximation for the portion of the data set from cycle CAC+1 to the end cycle for the PCR data set of FIG. 4A wherein the approximation is determined using a Levenberg-Marquardt regression process to determine the parameters of a double sigmoid function. The double sigmoid estimation step returns an estimated fluorescence level at cycle CAC+1. It also corrects the data for spikes present on the curve between cycle CAC+1 and the last cycle.

In step 125, the temperature shift is determined by calculating the difference of the fluorescence levels at cycle CAC+1 computed with the robust linear regression and the robust double sigmoid estimation is determined. This value is subtracted from the data points starting at cycle 1 to cycle CAC for the temperature shift correction in step 128. FIG. 4C shows an example of the temperature shift corrected data for the data set shown in FIGS. 4A and 4B.

In optional step 130, the spike removal process (e.g., a Levenberg-Marquardt Spike removal process) is performed using the shift-corrected data to detect and correct any spike(s) remaining (in particular, spike(s) in the baseline region of the step-corrected curve). As will be discussed in more detail below, FIG. 6 illustrates the process flow for identifying and replacing spike points in datasets representing PCR or other growth curves. A more detailed description of a process for determining and removing or replacing spike points can be found in U.S. patent application Ser. No. 11/316,315, titled "Levenberg Marquardt Outlier Spike Removal Method," US, filed on Dec. 20, 2005, the disclosure of which is incorporated by reference in its entirety.

In step 135, the modified, shift-corrected data set is returned, e.g., for display as shown in FIG. 4C or further processing. For example, in step 140, the normalized curve is then processed to determine the Ct value, and the result (shift-corrected data and/or Ct value) is returned, for example to the system that performed the analysis, or to a separate system that requested the analysis. Graphical displays may be rendered with a display device, such as a monitor screen or printer, coupled with the system that performed the analysis of FIG. 3, or data may be provided to a separate system for rendering on a display device. The Ct value may be determined according to various methods using the shift-corrected data set. For example, in one aspect, the teachings of U.S. patent application Ser. Nos. 11/316315 and 11/349550, each of which is hereby incorporated by reference, can be used to determine the Ct value.

Robust Linear Regression

The temperature change occurs in the baseline region of a PCR curve. Typically, the baseline region of a PCR curve can be approximated with a linear function of the form $f(x)=\text{slope}\cdot x+\text{intercept}$ where x represent the cycle number. To find the best values for the variables slope and intercept of the linear approximation, a robust linear regression is used in one aspect. Other regression methods or fit functions may be used, however, a robust linear fit is preferred to other methods, e.g., a least squares fit, to minimize the influence that artifacts such as spikes have on the quality of the regression.

According to one aspect, a robust linear regression minimizes the quantity $$\sum_{i=1}^{N} |y_i - \text{intercept} - \text{slope}\cdot x_i| \quad (1)$$

and for a fixed value of the slope, the value of the intercept that minimizes equation (1) is $$\text{intercept}=\text{median}\{y_i-\text{slope}\cdot x_i\} \quad (2)$$

The value of the slope can then be found as the root of the equation:

$$0 = \sum_{i=1}^{N} x_i \cdot sgn(y_i - \text{intercept} - \text{slope}\cdot x_i) \quad (3)$$

where sgn( ) is the sign function defined as $x>0, sgn(x)=1$ $x=0, sgn(x)=0$ $x<0, sgn(x)=-1$.

After substituting equation (2) into equation (3), there is one equation with one unknown to solve. In certain aspects, a bisection method is used to solve the resulting equation.

A bisection method is a root-finding algorithm which works by repeatedly dividing an interval in half and selecting the subinterval where the root exists. The bisection method is used in the robust linear regression of the present invention to solve the equation $$0 = \sum_{i=1}^{N} x_i \cdot sgn(y_i - \text{median}\{y_i - \text{slope}\cdot x_i\} - \text{slope}\cdot x_i) \quad (4)$$

where $x_i$ is the cycle number and $y_i$ is the fluorescence level at cycle $x_i$, and N=CAC. The bisection method is used to find the value of the slope variable for which equation (4) is minimized: this variable represents the slope of the baseline in a PCR curve, and in certain apsects takes values in the [−0.2; 0.2] interval. A typical shape of the function in equation (4) is shown in FIG. 5.

The bisection method converges linearly, which can be slow, but is guaranteed to converge if the interval considered contains a root. In one aspect, the initial convergence interval is defined as [−0.2;0.2] and 100 iterations of the bisection algorithm are performed. It should be appreciated that smaller or larger intervals may be used, and the greater or fewer iterations may be performed.

An example of Mathematica™ code for performing a bisection method according to aspects of the present invention is provided below.

```
abValue[data_] :=Module[{ },
    RSum[b_] :=Sum[(data[[i, 1]]*Sign[(data[[i, 2]] -
    a[b] - b data[[i, 1]])]),
        {i, 1, Length[data]}];
        a[b_] :=Median[Table[(data[[i, 2]] - b data[[i, 1]]),
        {i, 1, Length[data]}]];
    Lx = -0.2;
    Rx = 0.2;
    RsumL = RSum[Lx];
    RsumR = RSum[Rx];
    Nx = (Lx + Rx) / 2;
    RsumNx = RSum[Nx];
    For[i = 1, i ≦ 100, i++,
    {
        If[RsumL < 0 && RsumNx > 0, Rx = Nx];
        If[RsumL < 0 && RsumNx < 0, Lx = Nx];
        If[RsumL > 0 && RsumNx < 0, Rx = Nx];
        If[RsumL > 0 && RsumNx > 0, Lx = Nx];
        RsumL = RSum[Lx];
        RsumR = RSum[Rx];
        Nx = (Lx + Rx) / 2;
        PT[[i, 1]] = i;
        PT[[i, 2]] = Lx;
        PT[[i, 3]] = Rx;
        RsumNx = RSum[Nx];
    }]
]
```

LM Regression Process

As mentioned above, FIG. 6 illustrates the process flow for identifying and replacing spike points in datasets representing PCR or other growth curves. Steps 502 through 524 of FIG. 6 also illustrate a process flow for approximating the curve of a dataset and determining the parameters of a fit function. In one embodiment, a Levenberg-Marquardt (LM) method is used to calculate a robust curve approximation of a data set on the curve points from cycle CAC+1 to the last cycle. The LM regression is used to compute an estimate of the fluorescence level at cycle CAC+1 in order to minimize the influence that artifacts like spikes could have on the quality of the estimation. The LM method is a non-linear regression process; it is an iterative technique that minimizes the distance between a non-linear function and a data set. The process behaves like a combination of a steepest descent process and a Gauss-Newton process: when the current approximation doesn't fit well it behaves like the steepest descent process (slower but more reliable convergence), but as the current approximation becomes more accurate it will then behave like the Gauss-Newton process (faster but less reliable convergence).

In general, the LM regression method includes an algorithm that requires various inputs and provides output. In one aspect, the inputs include a data set to be processed, a function that is used to fit the data, and an initial guess for the parameters or variables of the function. The output includes a set of parameters for the function that minimizes the distance between the function and the data set.

According to one embodiment, the fit function is a double sigmoid of the form:

$$f(x) = a + bx + \frac{c}{(1 + \exp^{-d(x-e)})(1 + \exp^{-f(x-g)})}. \quad (5)$$

The choice of this equation as the fit function is based on its flexibility and its ability to fit the different curve shapes that a typical PCR curve or other growth curve may take. One skilled in the art will appreciate that variations of the above fit function or other fit functions may be used as desired.

The double sigmoid equation (5) has 7 parameters: a, b, c, d, e, f and g. The equation can be decomposed into a sum of a constant, a slope and a double sigmoid. The double sigmoid itself is the multiplication of two sigmoids. FIG. 7 illustrates a decomposition of the double sigmoid equation (5). The parameters d, e, f and g determine the shape of the two sigmoids. To show their influence on the final curve, consider the single sigmoid:

$$\frac{1}{1 + \exp^{-d(x-e)}}, \quad (6)$$

where the parameter d determines the "sharpness" of the curve and the parameter e determines the x-value of the inflexion point. FIG. 8 shows the influence of the parameter d on the curve and of the parameter e on the position of the x value of the inflexion point. Table 1, below, describes the influence of the parameters on the double sigmoid curve.

TABLE 1

Double sigmoid parameters description

| Parameter | Influence on the curve |
|---|---|
| a | Value of y at x = 0 |
| b | baseline and plateau slope |
| c | AFI of the curve |
| d | "sharpness" of the first sigmoid (See FIG. 9) |
| e | position of the inflexion point of the first sigmoid (See FIG. 10) |
| f | "sharpness" of the second sigmoid |
| g | position of the inflexion point of the second sigmoid |

In one aspect, the "sharpness" parameters d and f of the double sigmoid equation should be constrained in order to prevent the curve from taking unrealistic shapes. Therefore, in one aspect, any iterations where d<−1 or d>1.1 or where f<−1 or f>1.1 is considered unsuccessful. In other aspects, different constraints on parameters d and f may be used.

Because the Levenberg-Marquardt algorithm is an iterative algorithm, an initial guess for the parameters of the function to fit is typically needed. The better the initial guess, the better the approximation will be and the less likely it is that the algorithm will converge towards a local minimum. Due to the complexity of the double sigmoid function and the various shapes of PCR curves or other growth curves, one initial guess for every parameter may not be sufficient to prevent the algorithm from sometimes converging towards local minima. Therefore, in one aspect, multiple (e.g., three or more) sets of initial parameters are input and the best result is kept. In one aspect, most of the parameters are held constant across the multiple sets of parameters used; only parameters c, d and f may be different for each of the multiple parameter sets. FIG. 9 shows an example of the three curve shapes for the different parameter sets. The choice of these three sets of parameters is indicative of three possible different shapes of curves representing PCR data. It should be understood that more than three sets of parameters may be processed and the best result kept.

As shown in FIG. 6, the initial input parameters of the LM method are identified in step 510. These parameters may be input by an operator or calculated. According to one aspect, the parameters are determined or set according to steps 502, 504 and 506 as discussed below.

Calculation of Initial Parameter (a):

The parameter (a) is the height of the baseline; its value is the same for all sets of initial parameters. In one aspect, in step 504 the parameter (a) is assigned the 3rd lowest y-axis value, e.g., fluorescence value, from the data set. This provides for a robust calculation. In other aspects, of course, the parameter (a) may be assigned any other fluorescence value as desired such as the lowest y-axis value, second lowest value, etc.

Calculation of Initial Parameter (b):

The parameter (b) is the slope of the baseline and plateau. Its value is the same for all sets of initial parameters. In one aspect, in step 502 a static value of 0.01 is assigned to (b) as ideally there shouldn't be any slope. In other aspects, the parameter (b) may be assigned a different value, for example, a value ranging from 0 to about 0.5. In one aspect, the value (b) represents the baseline slope from CAC+1 to the end of the baseline.

Calculation of Initial Parameter (c):

The parameter (c) represents the height of the plateau minus the height of the baseline, which is denoted as the absolute fluorescence increase, or AFI. In one aspect, for the first set of parameters, c=AFI+2, whereas for the last two parameters, c=AFI. This is shown in FIG. 9, where for the last two sets of parameters, c=AFI. For the first set of parameters, c=AFI+2. This change is due to the shape of the curve modeled by the first set of parameters, which doesn't have a plateau.

Calculation of Parameters (d) and (f):

The parameters (d) and (f) define the sharpness of the two sigmoids. As there is no way of giving an approximation based on the curve for these parameters, in one aspect three static representative values are used in step 502. It should be understood that other static or non-static values may be used for parameters (d) and/or (f). These pairs model the most common shapes on PCR curves encountered. Table 2, below, shows the values of (d) and (f) for the different sets of parameters as shown in FIG. 9.

TABLE 2

Values of parameters d and f

| Parameter set number | Value of d | Value of f |
|---|---|---|
| 1 | 0.1 | 0.7 |
| 2 | 1.0 | 0.4 |
| 3 | 0.35 | 0.25 |

Calculation of Parameters (e) and (g):

In step 506, the parameters (e) and (g) are determined. The parameters (e) and (g) define the inflexion points of the two sigmoids. In one aspect, they both take the same value across all the initial parameter sets. Parameters (e) and (g) may have the same or different values. To find an approximation, in one aspect, the x-value of the first point above the mean of the intensity, e.g., fluorescence, (which isn't a spike) is used. A process for determining the value of (e) and (g) according to this aspect is shown in FIG. 10 and discussed below. A more detailed description of the process for determining the value of the parameters (e) and (g), and other parameters, according to this aspect can be found in U.S. patent application Ser. No. 11/316,315, US, filed on Dec. 20, 2005, the disclosure of which was previously incorporated by reference in its entirety.

With reference to FIG. 10, initially, the mean of the curve (e.g., fluorescence intensity) is determined. Next, the first data point above the mean is identified. It is then determined whether:

a. that point does not lie near the beginning, e.g., within the first 5 cycles, of the curve;

b. that point does not lie near the end, e.g., within the 5 last cycles, of the curve; and c. the derivatives around the point (e.g., in a radius of 2 points around it) do not show any change of sign. If they do, the point is likely to be a spike and should therefore be rejected.

Table 3, below, shows examples of initial parameter values as used in FIG. 9 according to one aspect.

TABLE 3

Initial parameters values:

| | Initial parameter set number | | |
|---|---|---|---|
| | 1 | 2 | 3 |
| Value of a | $3^{rd}$ lowest fluorescence value | $3^{rd}$ lowest fluorescence value | $3^{rd}$ lowest fluorescence value |
| Value of b | 0.01 | 0.01 | 0.01 |
| Value of c | $3^{rd}$ highest fluorescence value - a + 2 | $3^{rd}$ highest fluorescence value - a | $3^{rd}$ highest fluorescence value - a |
| Value of d | 0.1 | 1.0 | 0.35 |
| Value of e | X of the first non-spiky point above the mean of the fluorescence | X of the first non-spiky point above the mean of the fluorescence | X of the first non-spiky point above the mean of the fluorescence |
| Value of f | 0.7 | 0.4 | 0.25 |
| Value of g | X of the first non-spiky point above the mean of the fluorescence | X of the first non-spiky point above the mean of the fluorescence | X of the first non-spiky point above the mean of the fluorescence |

Returning to FIG. 6, once all the parameters are set in step 510, a LM process 520 is executed using the input data set, function and parameters. Traditionally, the Levenberg-Marquardt method is used to solve non-linear least-squares problems. The traditional LM method calculates a distance measure defined as the sum of the square of the errors between the curve approximation and the data set. However, when minimizing the sum of the squares, it gives outliers an important weight as their distance is larger than the distance of non-spiky data points, often resulting in inappropriate curves or less desirable curves. Therefore, according to one aspect of the present invention, the distance between the approximation and the data set is computed by minimizing the sum of absolute errors as this does not give as much weight to the outliers. In this aspect, the distance between the approximation and data is given by:

$$\text{distance} = \Sigma |y_{data} - y_{approximation}|. \quad (7)$$

As above, in one aspect, each of the multiple (e.g., three) sets of initial parameters are input and processed and the best result is kept as shown in steps 522 and 524, where the best result is the parameter set that provides the smallest or minimum distance in equation (7). In one aspect, most of the parameters are held constant across the multiple sets of parameters; only c, d and f may be different for each set of parameters. It should be understood that any number of initial parameter sets may be used.

Figure 11:
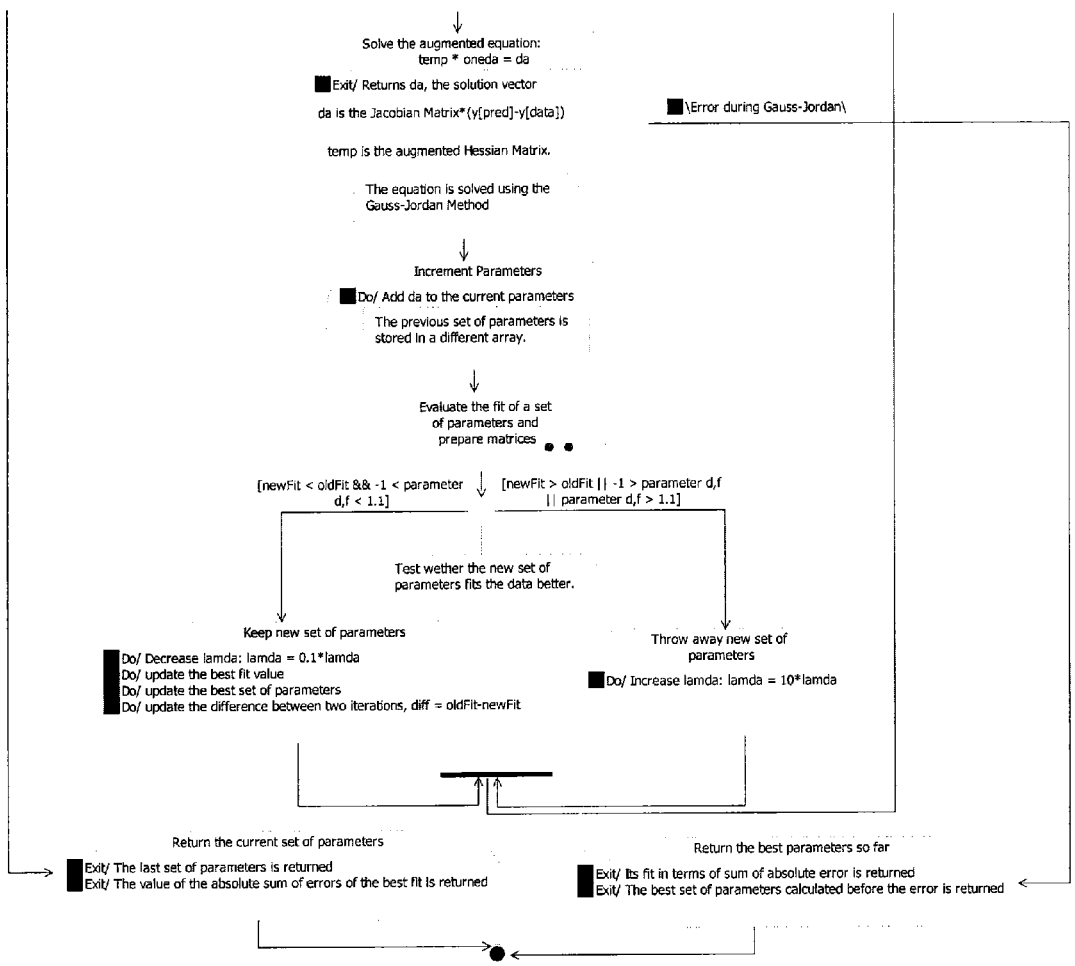
FIG. 11 illustrates a process flow of a Levenberg-Marquardt regression process for an initial set of parameters.

FIG. 11 illustrates a process flow of LM process 520 for a set of parameters according to the present invention. As explained above, the Levenberg-Marquardt method can behave either like a steepest descent process or like a Gauss-Newton process. Its behavior depends on a damping factor $\lambda$. The larger $\lambda$ is, the more the Levenberg-Marquardt algorithm will behave like the steepest descent process. On the other hand, the smaller $\lambda$ is, the more the Levenberg-Marquardt algorithm will behave like the Gauss-Newton process. In one aspect, $\lambda$ is initiated at 0.001. It should be appreciated that $\lambda$ may be initiated at any other value, such as from about 0.000001 to about 1.0.

As stated before, the Levenberg-Marquardt method is an iterative technique. According to one aspect, as shown in FIG. 11 the following is done during each iteration:

1. The Hessian Matrix (H) of the precedent approximation is calculated.
2. The transposed Jacobian Matrix ($J^T$) of the precedent approximation is calculated.
3. The distance vector (d) of the precedent approximation is calculated.
4. The Hessian Matrix diagonal is augmented by the current damping factor $\lambda$:

$$H_{aug} = H\lambda \quad (8)$$

5. Solve the augmented equation:

$$H_{aug}x = J^T d \quad (9)$$

6. The solution x of the augmented equation is added to the parameters of the function.
7. Calculate the distance between the new approximation and the curve.
8. If the distance with this new set of parameters is smaller than the distance with the previous set of parameters:
   The iteration is considered successful.
   Keep or store the new set of parameters.
   Decrease the damping factor $\lambda$, e.g., by a factor 10.
   If the distance with this new set of parameters is larger than the distance with the previous set of parameters:
   The iteration is considered unsuccessful.
   Throw away the new set of parameters.
   Increase the damping factor $\lambda$, e.g., by a factor of 10.

In one aspect, the LM process of FIG. 11 iterates until one of the following criteria is achieved:

1. It has run for a specified number, N, of iterations. This first criterion prevents the algorithm from iterating indefinitely. For example, in one aspect as shown in FIG. 10, the default iteration value N is 100. 100 iterations should be plenty for the algorithm to converge if it can converge. In general, N can range from fewer than 10 to 100 or more.
2. The difference of the distances between two successful iterations is smaller than a threshold value. e.g., 0.0001. When the difference becomes very small, the desired precision has been achieved and continuing to iterate is pointless as the solution won't become significantly better.
3. The damping factor $\lambda$ exceeds a specified value, e.g., is larger than $10^{20}$. When $\lambda$ becomes very large, the algorithm won't converge any better than the current solution, therefore it is pointless to continue iterating. In general, the specified value can be significantly smaller or larger than $10^{20}$.

EXAMPLES

Figure 12:
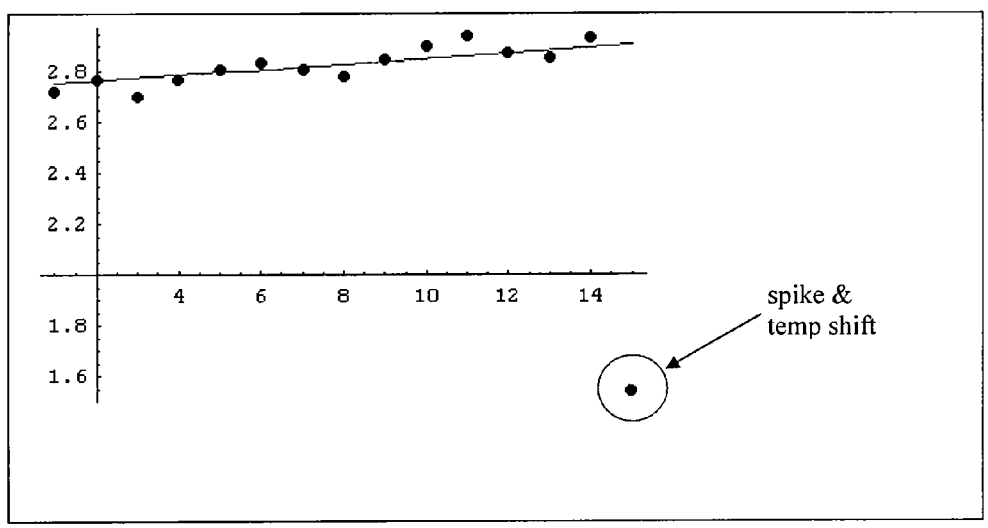
FIG. 12 shows the results of applying a robust linear regression to the data points from cycle 1 to cycle CAC.

Applying a robust linear regression to the data points from cycle 1 to cycle CAC for the growth curve results in the plot shown in FIG. 12. It is seen that the quality of the curve fit is excellent, as neither the temperature shift nor the spike influences the final result. Both the robust linear regression and the double sigmoid are then used to estimate the value of the fluorescence signal at the CAC+1, which in this case is cycle 16. The difference between these values is then used for the step correction. Note that it would be equally valid to estimate the robust linear approximation at cycle CAC and extrapolate the double sigmoid to the CAC value to determine the difference. In this data set, the estimated value of robust linear equation at cycle 16 is:

left=2.91669

The estimated value of robust double sigmoid at cycle 16 is:

right=2.11582 and the difference is:

dif=left−right=0.800866

Figure 13A:
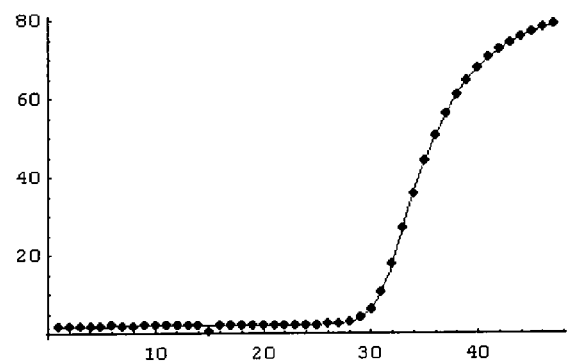
FIGS. 13A and 13B (expanded scale) show the complete PCR data set after temperature shift correction.
Figure 13B:
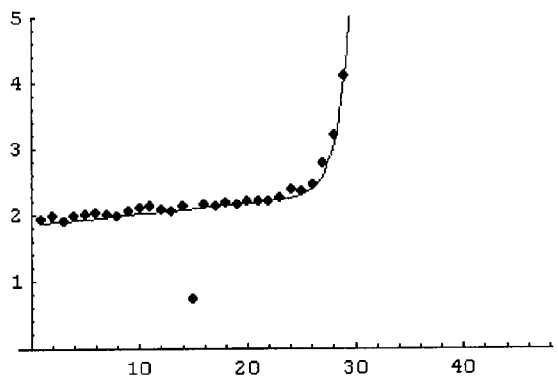
Figure 14:
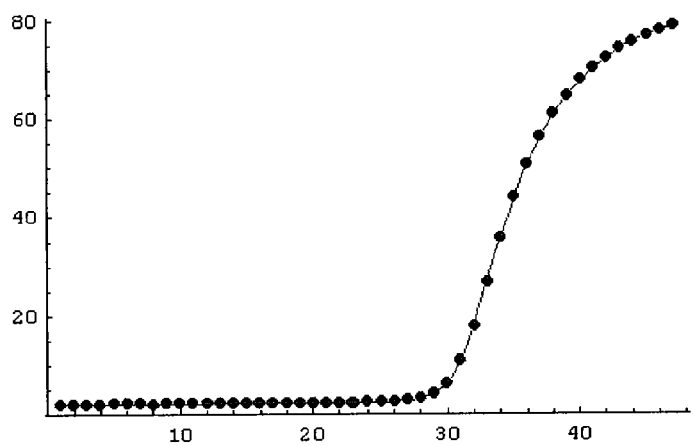
FIG. 14 shows the final curve after spike point removal.

The value of difference is then subtracted from the fluorescence signals for the portion of the data set corresponding to cycles 1 to CAC. The complete data set, after adjustment, is shown in FIGS. 13A and 13B (expanded scale), together with a double sigmoid Levenberg-Marquardt curve fit. The LM method, in one aspect, is then used to remove the outlier at cycle 15. The final curve, with a replacement point inserted at cycle 15 is shown in FIG. 14. The spike and fluorescent intensity change due to the annealing temperature change are now corrected.

It should be appreciated that the Ct determination processes, including the curve approximation and regression processes, may be implemented in computer code running on a processor of a computer system. The code includes instructions for controlling a processor to implement various aspects and steps of the Ct determination processes. The code is typically stored on a hard disk, RAM or portable medium such as a CD, DVD, etc. Similarly, the processes may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known.

One skilled in the art should appreciate that the various processes of the present invention can be coded using a variety of programming languages such as C, C++, C#, Fortran, VisualBasic, etc., as well as applications such as Mathematica which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, where multiple temperature step corrections are made, multiple regressions can be performed on different portions of the data set. For example, where two temperature shifts in the baseline portion of PCR data are made, a linear regression may be applied to a data set portion comprising cycle 1 to cycle of first change, and a second linear regression may be applied to the portion of the data set for the cycle of first change to cycle of second change, and a LM method may be applied to the data set for the cycle of second change to end cycle. Therefore, the scope of the appended claims should be accorded the broadest interpretation so as to encompass all such modifications and similar arrangements.

What is claimed is:

1. A computer-implemented method of correcting for temperature step changes in a data set for a Polymerase Chain Reaction (PCR) growth curve having a baseline portion and a growth portion, the method comprising the steps, implemented in a computer system having a processor, of:
   receiving a data set for a PCR growth curve, wherein said data set includes a plurality of data points for a kinetic Polymerase Chain Reaction (PCR) process, each data point having a pair of coordinate values (x,y), wherein x represents the cycle number and y represents an accumulation of amplified polynucleotide;
   calculating a linear approximation to a first portion of the curve, said first portion including data points in the data set including cycle numbers less than or equal to a cycle number (CAC) at which an annealing temperature change occurs in the PCR process;
   estimating a first y value for a first x value using the linear approximation of the first portion of the curve;
   calculating an approximation to a second portion of the curve by applying a Levenberg-Marquardt (LM) regression process to a second portion of the data set and a double sigmoid function to determine parameters of the function, said second portion of the data set including data points having cycle numbers greater than the CAC;
   estimating a second y value for the first x value using the approximation calculated for the second portion of the curve;
   determining a difference between the first and second y values; and
   subtracting off the difference from each y value for the data points corresponding to the first portion of the curve to produce a modified data set.

2. The method of claim 1, wherein the first x value is x=CAC+1.

3. The method of claim 1, wherein the first x value is x=CAC.

4. The method of claim 1, further including:
   determining whether one or more data points corresponding to the first portion of the data curve are outlier spikes by applying a LM regression process to the modified data set; and
   removing or replacing the data values for an identified spike from the modified data set.

5. The method of claim 1, wherein the CAC data point is included in the first portion of the data.

6. The method of claim 1, wherein the step of calculating a linear approximation includes applying a robust linear regression to the first portion of the curve.

7. The method of claim 6, wherein applying a robust linear regression includes applying a root finding method.

8. The method of claim 7, wherein the root finding method is a bisection method.

9. The method of claim 1, further comprising determining a cycle threshold (Ct) value using the modified data set.

10. The method of claim 1, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

11. The method of claim 1, wherein the double sigmoid function is of the form:

$$a + bx + \frac{c}{(1 + \exp^{-d(x-e)})(1 + \exp^{-f(x-g)})},$$

and wherein calculating includes iteratively determining one or more of the parameters a, b, c, d, e, f and g of the function.

12. A tangible computer-readable medium that stores code for controlling a processor to correct for temperature step changes in a data set for a Polymerase Chain Reaction (PCR) growth curve having a baseline portion and a growth portion, the code including instructions to:
   receive a data set for a PCR growth curve, wherein said data set includes a plurality of data points for a kinetic Polymerase Chain Reaction (PCR) process, each data point having a pair of coordinate values (x,y), wherein x represents the cycle number and y represents an accumulation of amplified polynucleotide;
   calculate a linear approximation to a first portion of the curve, said first portion including data points in the data set including cycle numbers less than or equal to a cycle number (CAC) at which an annealing temperature change occurs in the PCR process;
   estimate a first y value for a first x value using the linear approximation of the first portion of the curve;
   calculate an approximation to a second portion of the curve by applying a Levenberg-Marquardt (LM) regression process to a second portion of the data set and a double sigmoid function to determine parameters of the function, said second portion of the data set including data points having cycle numbers greater than the CAC;
   estimate a second y value for the first x value using the approximation calculated for the second portion of the curve;
   determine a difference between the first and second y values; and subtract off the difference from each y value for the data points corresponding to the first portion of the curve to produce a modified data set.

13. The computer-readable medium of claim 12, wherein the first x value is x=CAC+1.

14. The computer-readable medium of claim 12, wherein the first x value is x=CAC.

15. The computer-readable medium of claim 12, wherein the code further includes instructions to:
determine whether one or more data points corresponding to the first portion of the data curve are outlier spikes by applying a LM regression process to the modified data set; and
remove or replace the data values for an identified spike from the modified data set.

16. The computer-readable medium of claim 12, wherein the CAC data point is included in the first portion of the data.

17. The computer-readable medium of claim 12, wherein the instructions to calculate a linear approximation include instructions to apply a robust linear regression to the first portion of the curve.

18. The computer-readable medium of claim 17, wherein the instructions to apply a robust linear regression include instructions to apply a root finding process.

19. The computer-readable medium of claim 18, wherein the root finding process is a bisection method.

20. The computer-readable medium of claim 12, further including instructions to determine.a cycle threshold (Ct) value using the modified data set.

21. The computer-readable medium of claim 12, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

22. The computer-readable medium of claim 12, wherein the double sigmoid function is of the form:

$$a + bx + \frac{c}{(1 + \exp^{-d(x-e)})(1 + \exp^{-f(x-g)})},$$

and wherein the instructions to calculate include instructions to iteratively determine one or more of the parameters a, b, c, d, e, f and g of the function.

23. A kinetic Polymerase Chain Reaction (PCR) system, comprising:
a kinetic PCR data acquisition device that generates a PCR data set representing a kinetic PCR amplification curve having a baseline portion and a growth portion, wherein said data set includes a plurality of data points, each data point having a pair of coordinate values (x,y), wherein x represents the cycle number and y represents an accumulation of amplified polynucleotide; and
a processor adapted to receive and process the PCR dataset to correct for temperature step changes in the data set, by:
calculating a linear approximation to a first portion of the curve, said first portion including data points in the data set including cycle numbers less than or equal to a cycle number (CAC) at which an annealing temperature change occurs in the PCR process;
estimating a first y value for a first x value using the linear approximation of the first portion of the curve;
calculating an approximation to a second portion of the curve by applying a Levenberg-Marquardt (LM) regression process to a second portion of the data set and a double sigmoid function to determine parameters of the function, said second portion of the data set including data points having cycle numbers greater than the CAC;
estimating a second y value for the first x value using the approximation calculated for the second portion of the curve;
determining a difference between the first and second y values; and
subtracting off the difference from each y value for the data points corresponding to the first portion of the curve to produce a modified data set.

24. The kinetic PCR system of claim 23, wherein the kinetic PCR data acquisition device is a kinetic thermocycler device, and wherein the processor is communicably coupled to the data acquisition device.

25. The kinetic PCR system of claim 24, wherein the processor is resident in a computer system coupled to the data acquisition device over one of a network connection or a direct connection.

26. The kinetic PCR system of claim 23, wherein the first x value is x=CAC+1.

27. The kinetic PCR system of claim 23, wherein the first x value is x=CAC.

28. The kinetic PCR system of claim 23, wherein the intelligence module is adapted to:
determine whether one or more data points corresponding to the first portion of the data curve are outlier spikes by applying a LM regression process to the modified data set; and
remove or replace the data values for an identified spike from the modified data set.

29. The kinetic PCR system of claim 23, wherein the CAC data point is included in the first portion of the data.

30. The kinetic PCR system of claim 23, wherein calculating a linear approximation includes applying a robust linear regression to the first portion of the curve.

31. The kinetic PCR system of claim 30, wherein applying a robust linear regression includes applying a root finding process.

32. The kinetic PCR system of claim 31, wherein the root finding process is a bisection method.

33. The kinetic PCR system of claim 23, wherein the processor is adapted to determine a cycle threshold (Ct) value using the modified data set.

34. The kinetic PCR system of claim 23, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

35. The kinetic PCR system of claim 23, wherein the double sigmoid function is of the form:

$$a + bx + \frac{c}{(1 + \exp^{-d(x-e)})(1 + \exp^{-f(x-g)})},$$

and wherein calculating includes iteratively determining one or more of the parameters a, b, c, d, e, f and g of the function.

36. The computer readable medium of claim 12, wherein the tangible medium comprises one of a CD, a DVD, a hard disk, or a RAM.

* * * * *